United States Patent
Brooks et al.

(10) Patent No.: US 12,257,134 B2
(45) Date of Patent: Mar. 25, 2025

(54) TAMPON PRESS

(71) Applicant: Johnson & Johnson GmbH, Neuss (DE)

(72) Inventors: Nick Brooks, Warwick (GB); David L. Kimball, Flemington, NJ (US); Peter Morgan, Warwickshire (GB); James Stembridge, Warwickshire (GB)

(73) Assignee: Johnson & Johnson GmbH, Neuss (DE)

( * ) Notice: Subject to any disclaimer, the term of this patent is extended or adjusted under 35 U.S.C. 154(b) by 0 days.

(21) Appl. No.: 18/605,430

(22) Filed: Mar. 14, 2024

(65) Prior Publication Data

US 2024/0216184 A1 Jul. 4, 2024

Related U.S. Application Data

(62) Division of application No. 17/022,291, filed on Sep. 16, 2020, now Pat. No. 11,950,986.

(60) Provisional application No. 62/907,153, filed on Sep. 27, 2019.

(51) Int. Cl.
| | |
|---|---|
| *B29C 43/02* | (2006.01) |
| *A61F 13/20* | (2006.01) |
| *B30B 11/00* | (2006.01) |

(52) U.S. Cl.
CPC ...... *A61F 13/2088* (2013.01); *A61F 13/2091* (2013.01); *B29C 43/02* (2013.01); *B30B 11/007* (2013.01)

(58) Field of Classification Search
CPC .............. A61F 13/2082; A61F 13/2091; A61F 13/2088; A61F 13/2085; B29C 43/02; B29C 43/021; B30B 7/04; B30B 11/007
See application file for complete search history.

(56) References Cited

U.S. PATENT DOCUMENTS

| | | |
|---|---|---|
| 3,854,481 A | 12/1974 | Messing |
| 4,212,301 A | 7/1980 | Johnson |
| 4,326,527 A | 4/1982 | Wollangk et al. |
| 4,627,849 A | 12/1986 | Walton et al. |

(Continued)

FOREIGN PATENT DOCUMENTS

| | | |
|---|---|---|
| CN | 1531415 A | 9/2004 |
| EP | 1459720 A | 9/2004 |

(Continued)

OTHER PUBLICATIONS

International search report and written opinion dated Nov. 25, 2020, for international application PCT/EP2020/076935).

*Primary Examiner* — Thu Khanh T. Nguyen (57) ABSTRACT

A press for shaping an absorbent tampon blank into a shaped tampon pledget includes a central cavity arranged and configured to accommodate an absorbent tampon blank having a front portion and a back portion. The main longitudinal axis of the press passes in the middle of the central cavity and a plurality of penetrating dies are arranged radially around the said main longitudinal axis. Each penetrating die has a pressing face on at least a fragment of its side facing the central cavity. The said press comprises at least one cam to actuate the plurality of penetrating dies. Furthermore, the plurality of penetrating dies comprises at least one penetrating die having a pressing face with a first shaped longitudinal profile, and least one penetrating die having a pressing face with a second shaped longitudinal profile.

1 Claim, 10 Drawing Sheets

(56) References Cited

U.S. PATENT DOCUMENTS

| | | | |
|---|---|---|---|
| 5,153,971 A | 10/1992 | Van Iten | |
| 5,370,633 A | 12/1994 | Villalta | |
| 5,659,934 A | 8/1997 | Jessup et al. | |
| 6,310,269 B1 | 10/2001 | Friese et al. | |
| 7,120,977 B2 | 10/2006 | Bittner et al. | |
| 7,736,572 B2 | 6/2010 | Gilbert et al. | |
| 7,740,787 B2 | 6/2010 | Hubbard, Jr. et al. | |
| 7,867,209 B2 | 1/2011 | Jorgensen et al. | |
| 7,981,347 B2 | 7/2011 | Hubbard, Jr. et al. | |
| 8,082,639 B2 | 12/2011 | Rolli | |
| 8,293,968 B2 | 10/2012 | Schmidt-Först et al. | |
| 8,460,262 B2 | 6/2013 | Fung et al. | |
| 8,474,114 B2 | 7/2013 | Rolli | |
| 8,518,005 B2 | 8/2013 | Handel et al. | |
| 8,574,210 B2 | 11/2013 | Van Ingelgem et al. | |
| 8,684,987 B2 | 4/2014 | Hasse et al. | |
| 8,735,647 B2 | 5/2014 | Schoelling | |
| 8,827,975 B2 | 9/2014 | Kimball et al. | |
| 8,834,439 B2 | 9/2014 | Kimball et al. | |
| 9,155,666 B2 | 10/2015 | Smet et al. | |
| 9,622,919 B2 | 4/2017 | Pelley | |
| 9,795,518 B2 | 10/2017 | Pelley | |
| 2002/0151859 A1 | 10/2002 | Schoelling | |
| 2003/0176845 A1 | 9/2003 | Kollwitz | |
| 2004/0199137 A1 | 10/2004 | Lamb et al. | |
| 2004/0226152 A1 | 11/2004 | Prosise et al. | |
| 2005/0113787 A1 | 5/2005 | Carlin | |
| 2005/0193536 A1 | 9/2005 | Ingelgem et al. | |
| 2007/0234532 A1 | 10/2007 | Gilbert et al. | |
| 2008/0065041 A1 | 3/2008 | Stan et al. | |
| 2008/0119811 A1 | 5/2008 | Gilbert et al. | |
| 2008/0275417 A1 | 11/2008 | Gilbert et al. | |
| 2009/0082712 A1 | 3/2009 | Hasse et al. | |
| 2010/0102481 A1 | 4/2010 | Hubbard, Jr. et al. | |
| 2013/0018342 A1 | 1/2013 | Schmidt-Forst | |
| 2013/0072892 A1 | 3/2013 | Hasse et al. | |
| 2014/0000628 A1 | 1/2014 | Avery, Jr. et al. | |
| 2014/0088539 A1 | 3/2014 | Kimball | |
| 2014/0265026 A1 | 9/2014 | Schoelling | |
| 2014/0276523 A1 | 9/2014 | Schoelling | |
| 2021/0007904 A1 | 1/2021 | Kimball | |

FOREIGN PATENT DOCUMENTS

| | | |
|---|---|---|
| EP | 1459720 B | 4/2005 |
| EP | 1622556 B | 2/2006 |
| EP | 1759678 A | 3/2007 |
| EP | 1485054 B | 8/2007 |
| EP | 1622557 B | 11/2007 |
| EP | 1485055 B | 12/2007 |
| EP | 1601322 B | 12/2008 |
| EP | 1267782 B | 1/2012 |
| EP | 1485053 B | 10/2012 |
| EP | 2349158 B | 7/2013 |
| EP | 2712594 B | 9/2015 |
| EP | 2712596 B | 8/2016 |
| EP | 2900467 B | 6/2017 |
| EP | 2712595 B | 7/2017 |
| WO | WO 2004/080362 A | 9/2004 |
| WO | WO 2004/100846 A | 11/2004 |
| WO | WO 2004/100847 A | 11/2004 |
| WO | WO 2005/046548 A | 5/2005 |
| WO | WO 2005/046549 A | 5/2005 |
| WO | WO 2008/056339 A | 5/2008 |
| WO | WO 2009/040737 A | 4/2009 |
| WO | WO 2014/004798 A | 1/2014 |
| WO | WO 2018/220587 A | 12/2018 |

TAMPON PRESS

CROSS-REFERENCE TO RELATED APPLICATIONS

This application is a divisional of U.S. application Ser. No. 17/022,291 filed on Sep. 16, 2020 (now U.S. Pat. No. 11,950,986), which claims the benefit of U.S. Provisional application 62/907,153 filed Sep. 27, 2019, the complete disclosures of which are hereby incorporated herein by reference for all purposes.

FIELD OF THE INVENTION

The present invention relates to an intravaginal tampon for feminine hygiene. In particular, it relates to a press for producing such tampon having penetrating dies with shaped pressing faces; and to the tampons made therewith.

BACKGROUND OF THE INVENTION

Intravaginal tampons have been used for decades. Two types of tampons are present on the market, digital tampons and tampons requiring an applicator. Typically, digital tampons are formed by radial compression of a blank with a set of jaws while applicator tampons are formed by molding a blank. Both types of tampons have generally a cylindrical shape, and both have advantages and disadvantages.

Digital tampon can be inserted manually without an applicator, they have a neat smooth surface; however, the compression column created by the press jaw within the product to generate the rigidity required for digital insertion may be uncomfortable for some consumers. Applicator tampons may not have this rigidity issue; however, they require the use of an applicator and generate additional waste.

It is also important to consider that a tampon may change in position while in place depending on the activity of the wearer, e.g. moving, doing sports or even coughing. This can create discomfort and even leakage if the new position of the tampon is not adapted.

Leakage avoidance and wearing comfort are two important benefits for the consumer.

Shaped tampons have been proposed to fulfill these requirements. These existing shaped products are claimed to match more precisely the wearer anatomy and thus provide a better protection against by pass leakage, reduce discomfort and generally stay in place more efficiently within the vagina.

EP1267782B1 by the Procter & Gamble Company purport to disclose a cylindrical tampon that radially expands into an oval cross section shape when exposed to a wet environment. Tampon is rolled into an oval cross section blank which is compressed by a press jaw into a cylindrical tampon.

US20140265026A1 by Eveready Battery Company purport to disclose a tampon with spirally shaped longitudinal grooves and the press jaw for shaping said tampon.

U.S. Pat. No. 8,574,210B2 by Ontex Hygieneartikel Deutschland purport to disclose a tampon with longitudinal groves and a press jaw for shaping it.

EP1759678A1 by Ontex Hygieneartikel Deutschland purport to disclose a tampon with longitudinal groves and a press jaw for shaping a mushroom shaped tampon.

EP2900467A1 by Kimberly-Clark Worldwide purport to disclose a press jaw for tampon forming. Press jaw is designed to decrease the area of the compression surface in contact with the tampon as the press moves inward.

EP2712594B1EP, EP2712595B1 & EP2712596B1 by Johnson & Johnson purport to disclose tampon with deep intersecting grooves; said grooves are continuous in EP2712595B1, detached in EP2712596B1, or could represent 150% of the pledget length in EP2712594B1. Also disclosed is a tampon press with sets of adjacent jaws passing through the same press space during manufacture. Press jaws comprise two sets of penetrating dies, each set having a penetrating face corresponding to a groove segment shape.

While the above examples describe presses to produce tampon with different profiles or grooves configuration, these tampons have traditional cylindrical shapes.

Further the above examples fail to provide indications about the press configuration required to achieve a tampon with a complex longitudinal or radial shape.

SUMMARY OF THE INVENTION

It has been discovered that a shaped tampon with a shaped longitudinal profile and an elliptical cross section on at least a part of its length can provide a better fit to the wearer anatomy and thus increases the wearer comfort without compromising the fluid abortion properties.

In one aspect the present invention discloses a press for shaping an absorbent tampon blank into a shaped tampon pledget. Said press comprises a central cavity arranged and configured to accommodate an absorbent tampon blank having a front portion and a back portion. The main longitudinal axis of the press passes in the middle of the central cavity and a plurality of penetrating dies are arranged radially around the said main longitudinal axis. Each penetrating die has a pressing face on at least a fragment of its side facing the central cavity. The said press comprises at least one cam to actuate the plurality of penetrating dies. Furthermore, the plurality of penetrating dies comprises at least one penetrating die having a pressing face with a first shaped longitudinal profile, and least one penetrating die having a pressing face with a second shaped longitudinal profile.

In another aspect the present invention relates to a method for shaping a tampon comprising the steps of introducing a tampon blank in a press according to the present disclosure, actuating a first group of penetrating dies then actuating a second group of penetrating dies. Partially disengaging the first group of penetrating dies to a transfer position and allowing the front portion of a compressed tampon pledget to pass through said partially disengaged group of penetrating dies. Partially disengaging the second group of penetrating dies and ejecting compressed tampon pledget from the press to a carrier device.

In yet another aspect, the present invention relates to shaped tampons obtained by a press according to the present disclosure.

Other aspects and features of the present invention will become apparent in those ordinarily skilled in the art upon review of the following description of specific embodiments of the invention in conjunction with the accompanying drawings.

DETAILED DESCRIPTION OF THE PREFERRED EMBODIMENTS

As used in the specification and the claims, the term "shaped longitudinal profile" and variants thereof relate to the configuration of the edge of an object, considered along the longitudinal axis of the press. By "shaped" it is meant that the said edge of the object is not straight on its full length; it may be curved, possibly several times. In other words, the shaped profile may comprise concave or convex curves, alone or in a succession with one or more curves. It may also comprise one or more straight portions in association with one or more curved portion.

As used in the specification and the claims, the term "tampon blank" and variants thereof relate to an uncompressed tampon material.

As used in the specification and the claims, the term "pledget" and variants thereof relate to a pad or a compress of absorbent material such as fibers designed to absorb bodily fluids. A "tampon pledget" relates to the compressed absorbent material after compression of a tampon blank in a press.

In one embodiment, a press for shaping an absorbent tampon blank into a shaped tampon pledget has a central cavity, the main longitudinal axis of the press passing in the middle of the central cavity; a plurality of penetrating dies arranged radially around the said main longitudinal axis; and at least one cam to actuate the plurality of penetrating dies. The central cavity is arranged and configured to accommodate an absorbent tampon blank having a front portion and a back portion. Each penetrating die has a pressing face on at least a fragment of its side facing the central cavity. At least one penetrating die has a pressing face with a first shaped longitudinal profile, and at least one penetrating die has a pressing face with a second shaped longitudinal profile. The said front portion corresponds to the insertion tip of the tampon pledget, and the back portion corresponds to the withdrawal end of the tampon pledget. The said first shaped longitudinal profile and second shaped longitudinal profile may be different.

Having shaped longitudinal profiles on the penetrating die pressing faces enable the production of tampon pledget with shaped profile. When several different longitudinal profiles are used it becomes possible to create tampon pledgets with complex longitudinal profiles and potentially non-circular cross section on at least a portion of the tampon pledget. These shaped tampons are believed to provide enhanced comfort to the user by having a shape more adapted to the vaginal configuration, compared to straight cylindrical tampon.

Figure 1:
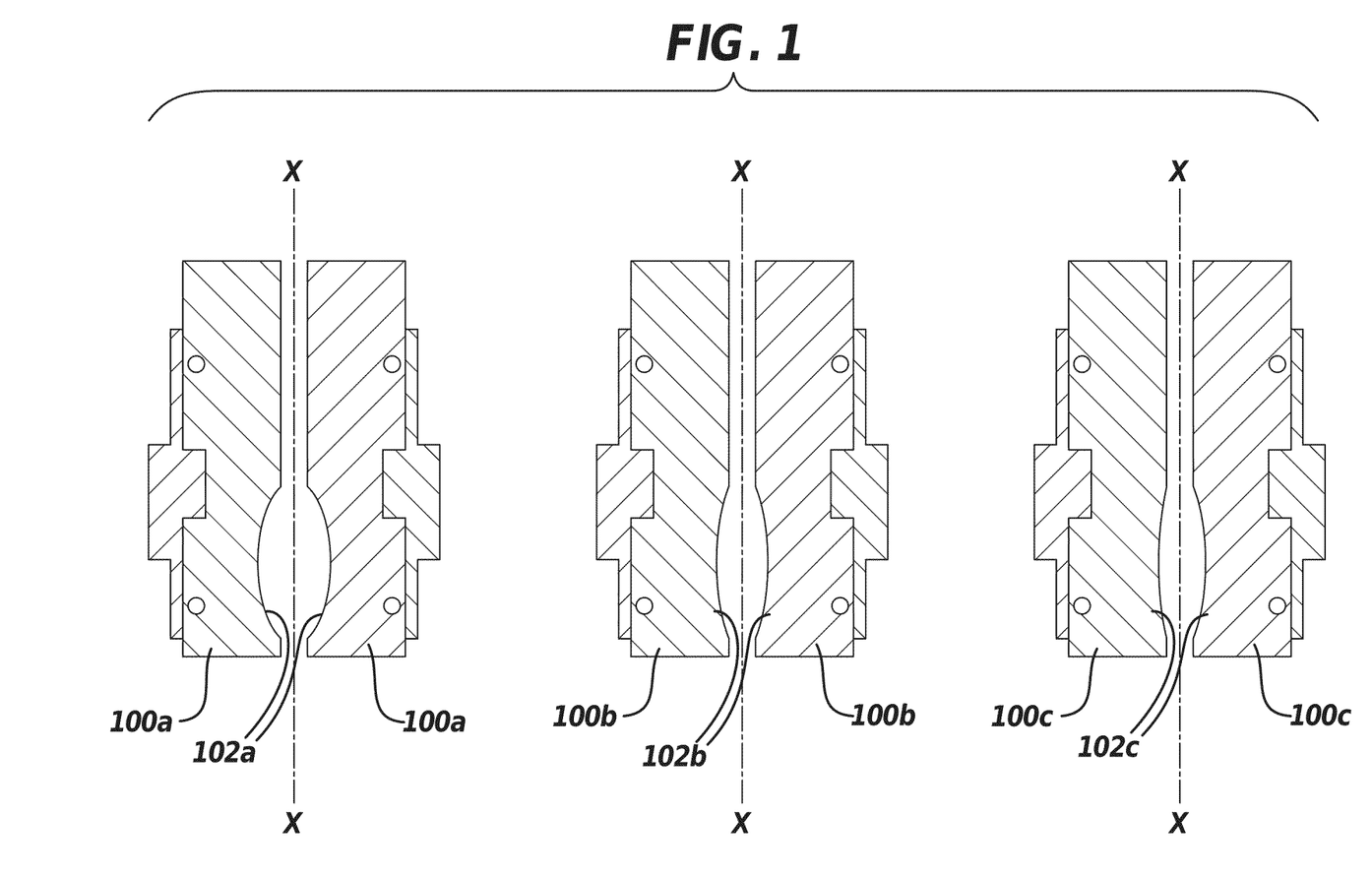
FIG. 1 is a side view of three embodiments of penetrating dies. For each embodiments a pair of dies are shown. Each embodiment has a different shaped profile.

FIG. 1 illustrates three pairs of penetrating dies 100a, 100b, 100c with their pressing face 102a, 102b, 102c having three different shaped profile embodiments of said pressing face pairs.

The plurality of penetrating dies may be arranged about the main longitudinal axis X-X in opposing sets of penetrating dies. In that configuration, at least one opposing sets of penetrating dies may be arranged to have the opposing pressing faces disposed at 180° according to the main longitudinal axis.

In a particular embodiment at least one opposing sets of penetrating dies may be arranged to have two pressing faces opposed to one pressing face; or as an alternative, to have one pressing face moving toward a gap between two other pressing faces, and opposing sets of penetrating dies may comprise an even or odd number of penetrating dies.

Figure 2:
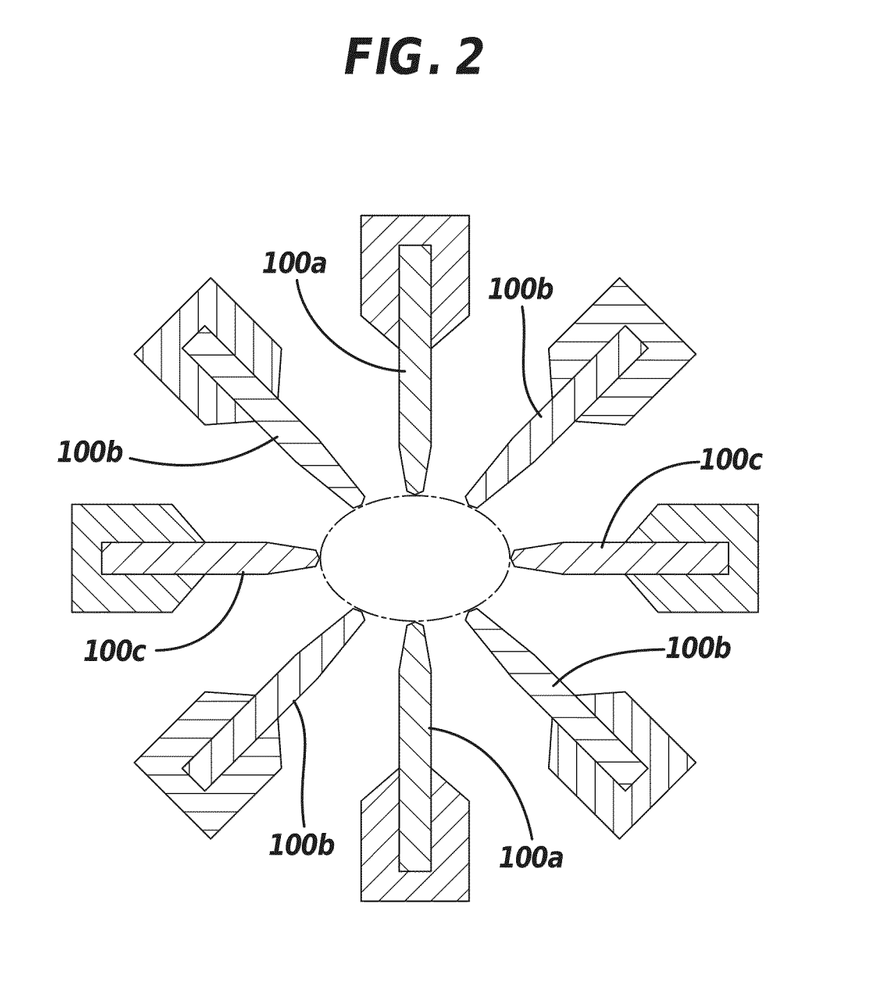
FIG. 2 is a radial view of a press comprising eight penetrating dies. By radial view it is meant according to a plane perpendicular to the main longitudinal axis.
Figure 3:
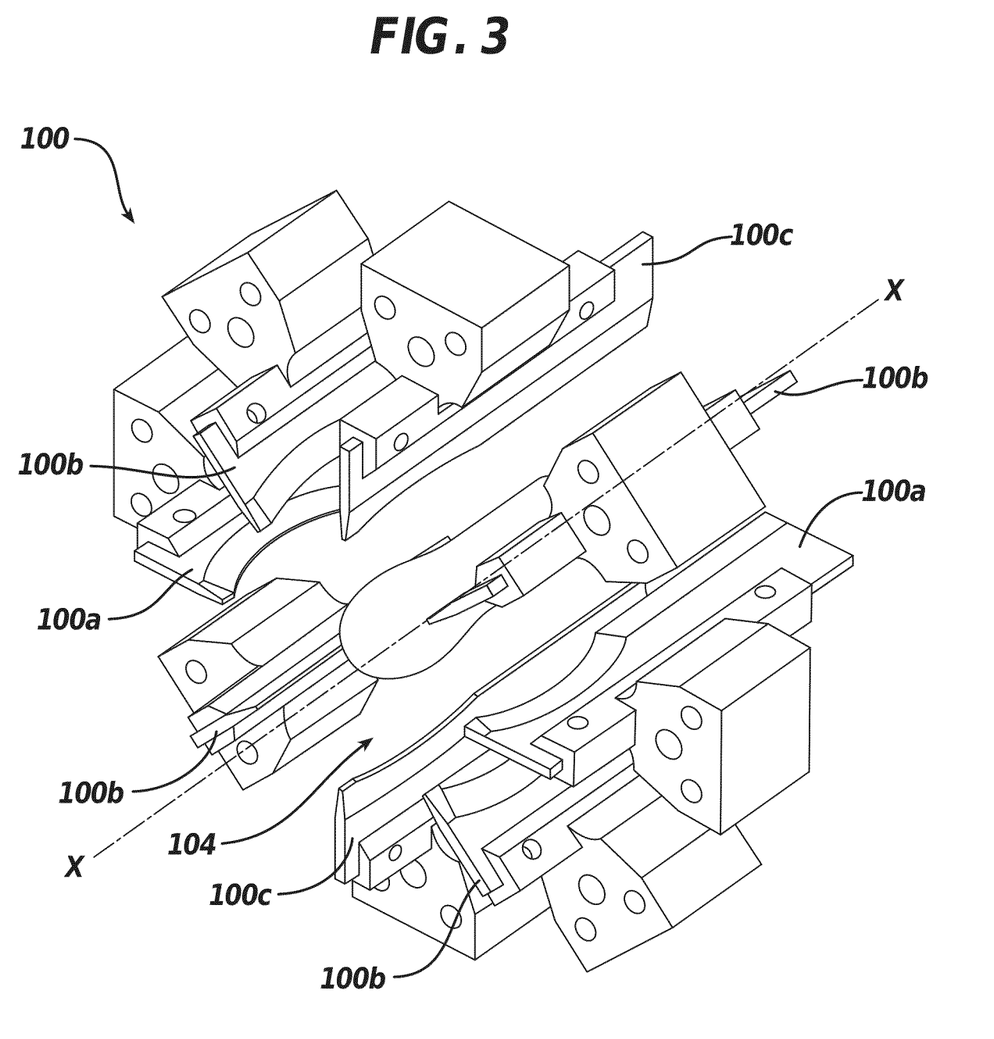
FIG. 3 is a perspective view of a press comprising eight penetrating dies and a compressed tampon. The penetrating dies are in an open configuration. For clarity the grooves have been omitted on the tampon.

Referring to FIGS. 2 and 3, three opposing sets of penetrating dies are represented radially arranged around the central cavity 104 of the press 100. A first opposing set of two penetrating dies 100a has a large maximum gap between opposed pressing faces 102a, a second opposing set of four penetrating dies 100b has an intermediate maximum gap between opposing pressing faces 102b, and a third opposing set of two penetrating dies 100c has the smallest maximum gap between opposing press faces 102c (as shown in FIG. 1).

Figure 4:
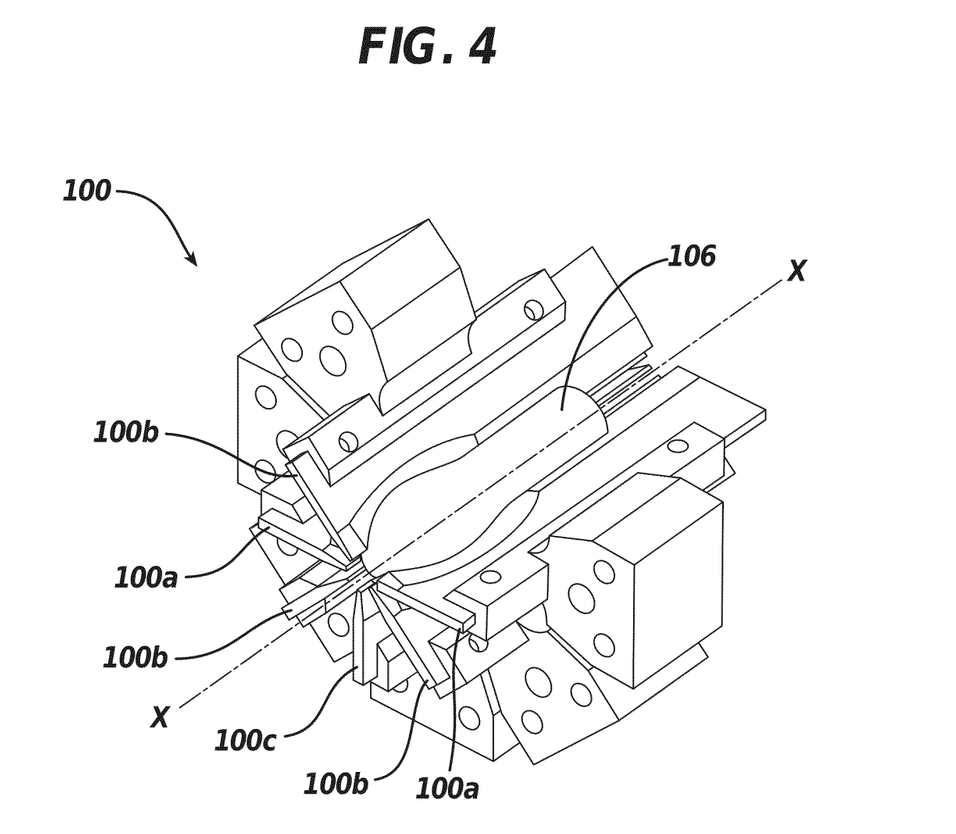
FIG. 4 is a perspective view corresponding to FIG. 3, the penetrating dies are in a closed configuration. For clarity two penetrating dies have been omitted so that the tampon is visible.

FIG. 4 corresponds to FIG. 3, with the penetrating dies engaged in the tampon pledget 106 along the longitudinal axis X-X. For clarity two penetrating dies have been omitted on FIG. 4.

Preferably, at least one opposing sets of penetrating dies may have an even number of penetrating dies. In a further preferred configuration, at least one opposing sets of penetrating dies may have at least four penetrating dies disposed around the main longitudinal axis.

The press according to the present invention may have an even number of opposing sets of penetrating dies. In another embodiment, such as illustrated in FIGS. 1-4, the press may have at least 3 different opposing sets of penetrating dies.

In a preferred configuration, within an opposed set of penetrating dies the groups of opposed pressing faces may be identical. In a further preferred configuration, such as illustrated in FIGS. 1-4, the pressing faces of an opposed set of penetrating dies may have an axial symmetry. In other words, within a preferred configuration, the pressing faces of said opposed set of penetrating dies may have at least one plane of symmetry, preferably two planes of symmetry.

In a second embodiment of the invention, a press for shaping absorbent tampon blank incorporates penetrating dies that are divided longitudinally, creating a group of composite penetrating dies. The composite penetrating dies have two parts: a front part and a back part. The front parts of the composite penetrating dies are grouped together and referred to as the front group. The back parts of the composite penetrating dies are grouped together and referred to as the back group.

The front group is arranged and configured to shape the insertion end of the tampon.

The back group is arranged and configured to shape the withdrawal end of the tampon.

The use of composite penetrating dies enables the creation of complex shaped tampon as the penetrating dies shaping the front portion and the back portion of the tampon blank may be different and can be operated in an un-simultaneous way. This may be relevant as the central cavity has a limited space and would only provide the possibility to operate a limited number of pressing faces at the same time.

Figure 5:
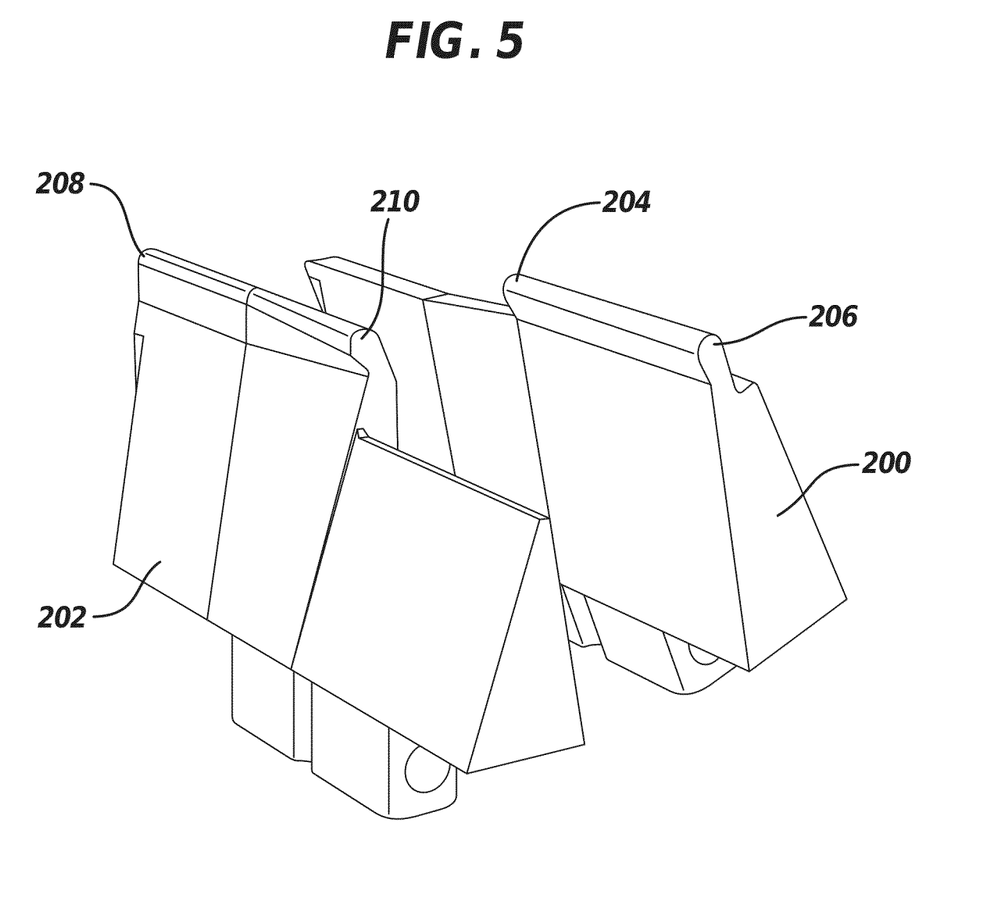
FIG. 5 is a perspective view of a split composite penetrating die. The front part is on the right side of the view, the back part is on the left part of the view. Pressing faces are pointing upward.
Figure 6A:
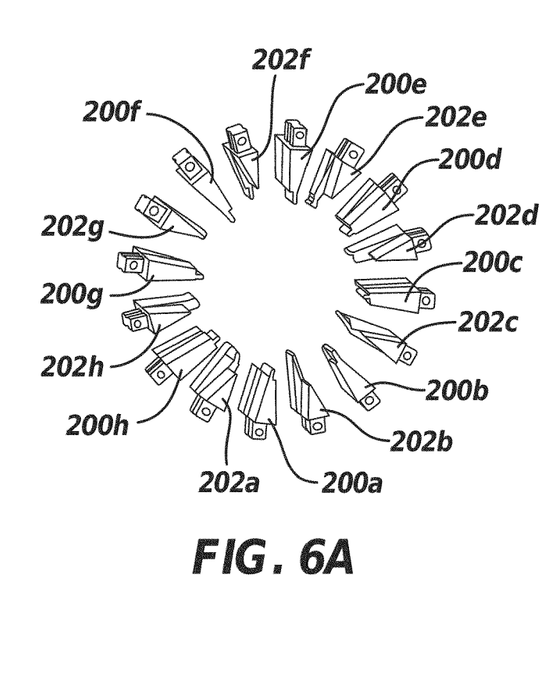
FIG. 6A is a perspective view of eight composite penetrating dies, arranged radially, in an open configuration.
Figure 6B:
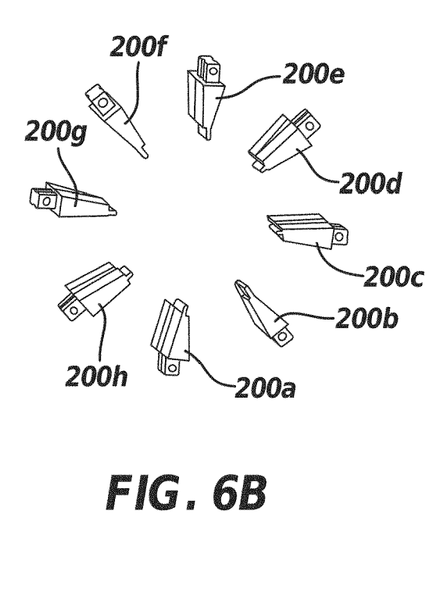
FIG. 6B is a perspective view corresponding to FIG. 6A, showing only the front part of the composites penetrating dies.
Figure 6C:
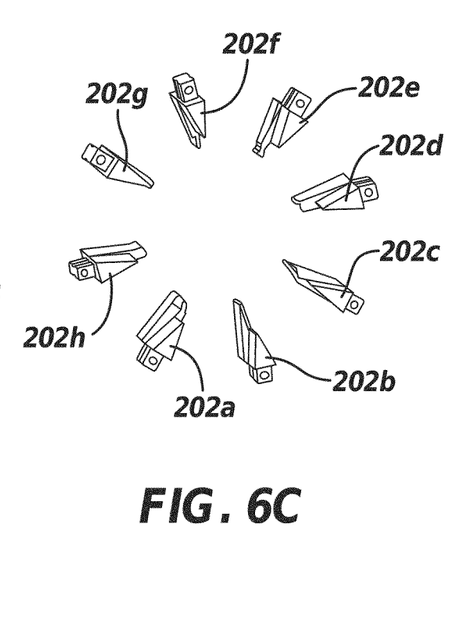
FIG. 6C is a perspective view corresponding to FIG. 6A, showing only the back part of the composites penetrating dies.
Figure 7A:
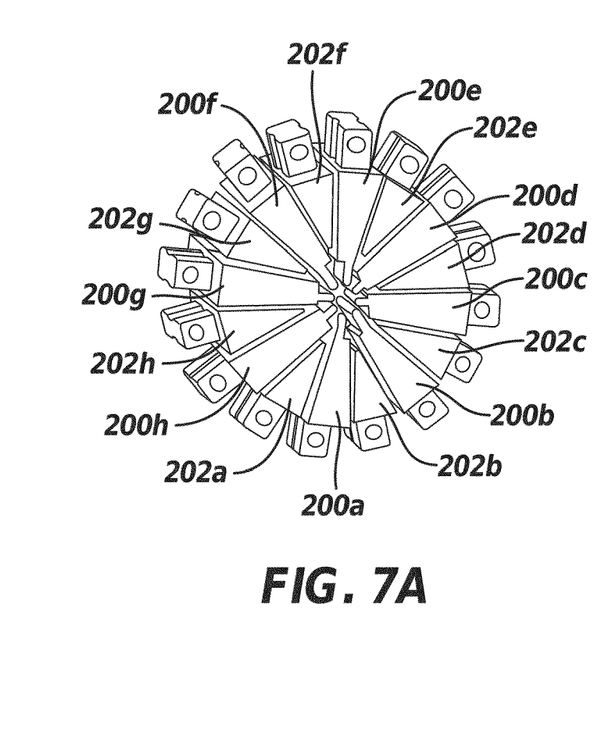
FIG. 7A is a perspective view of eight composite penetrating dies, arranged radially, in a closed configuration.
Figure 7B:
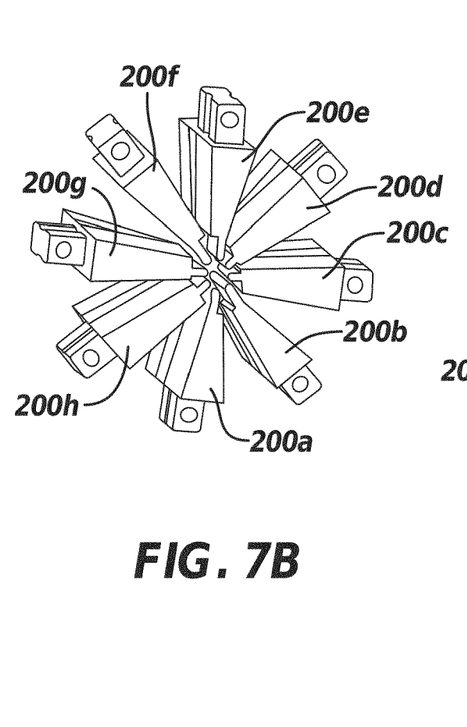
FIG. 7B is a perspective view corresponding to FIG. 6A, showing only the front part of the composites penetrating dies.
Figure 7C:
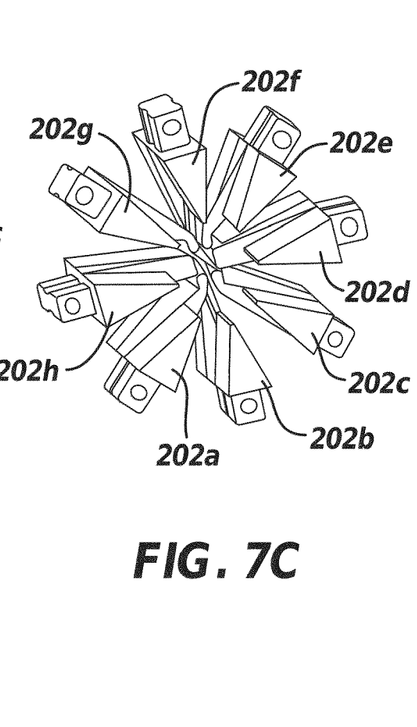
FIG. 7C is a perspective view corresponding to FIG. 6A, showing only the back part of the composites penetrating dies.

Referring to FIG. 5, it is shown an embodiment of a composite penetrating dies comprising a front part 200 and a back part 202. As shown in FIGS. 6A, 6B and 6C. All the composite penetrating dies front parts 200a-200h will constitute the front group (or composite penetrating dies front group) such as illustrated in FIG. 6B. Accordingly, all the composite penetrating dies back parts 202a-202h will constitute the back group (or composite penetrating dies back group) such as illustrated in FIG. 6C. FIG. 6A discloses how the front group and back group may be arranged along the longitudinal axis.

The above-described configuration of penetrating dies allows the front group and the back group to be actuated independently. This particular configuration allows more freedom in the operation of the press according to the invention and might be achieved, for example, a first cam operating the front group and a second cam operating the back group.

In an embodiment, all penetrating dies may be composite penetrating dies.

In an embodiment, at least two composite penetrating die front parts are identical e.g., 200c and 200g. Again, the said composite penetrating die front parts may be arranged by opposing sets.

In an embodiment, a press according the present invention may also comprise at least two composite penetrating die back parts that are identical, e.g., 202a and 202e. Again, the said composite penetrating die back parts may be arranged by opposing sets.

In an embodiment, the press has at least two of the composite penetrating dies that have a back part and front part pressing faces that are positioned to produce, on the outer surface of an absorbent tampon pledget, a substantially continuous groove made of two segments; the extremities the said two pressing faces being adjacent at a connection point.

As used in the specification and the claims, the term "groove" and variants thereof relate to an indentation in the surface of the tampon pledget. For clarification, grooves may be "penetrating grooves", extending at least 0.7 mm (or 10% of the radius, whichever is greater) into the tampon pledget or they may be "shallow grooves", primarily surface indentations without significant penetration (of no more than 0.7 mm, not more than 10% of the radius) into the tampon pledget body. Regions between grooves may take the form of ribs.

As used in the specification and the claims, the term "adjacent" and variants thereof relate to elements that are positioned side by side but not touching each other. It is preferable to have the extremities not touching each other as it would create a friction and heat and it might be detrimental for the proper operating of the press at high speed.

As used in the specification and the claims, the term "extremities" and variants thereof relate to the end of the pressing faces according to their narrow longitudinal dimension. Referring to FIG. 5, in this embodiment the two extremities 204, 206 of a composite penetrating die front part 200 and two extremities 208, 210 of a composite penetrating die back part 202 are indicated. Each pressing face would have two types of extremities: exterior extremities 206, 208 of the front part and back part, respectively and interior extremities 204, 210. The extremities considered in the present embodiment to form a substantially continuous groove are the two interior extremities 204, 210 as these act on the tampon blank and define a connection point of the ensuing groove.

Said connection point may be located approximately in the central portion of the tampon blank. By central portion it is meant 25% to 75% of the length of the tampon pledget, preferably 40% to 60% of the length of the tampon pledget; wherein the length is considered according to the longitudinal axis.

In a particular embodiment, the press has a plurality of the composite penetrating die back parts that have pressing faces that are not parallel to the main longitudinal axis, and preferably the said pressing faces are helically arranged. This configuration increases the length of the grooves thereby increasing the path of any fluid along the tampon and thus decreasing the risk of leakage.

In an alternative embodiment, all composite penetrating die front parts may have pressing faces that are parallel to the main longitudinal axis. This configuration may reduce the ejection forces necessary to remove the pledget from the press.

In another embodiment, a press according to the present invention may have at least two adjacent composite penetrating dies having front parts and back parts pressing faces that have no connection point. Thus, at least two composite penetrating dies may have front part and back part pressing faces that would not produce a substantially continuous groove on the outer surface of the tampon pledget.

Figure 8:
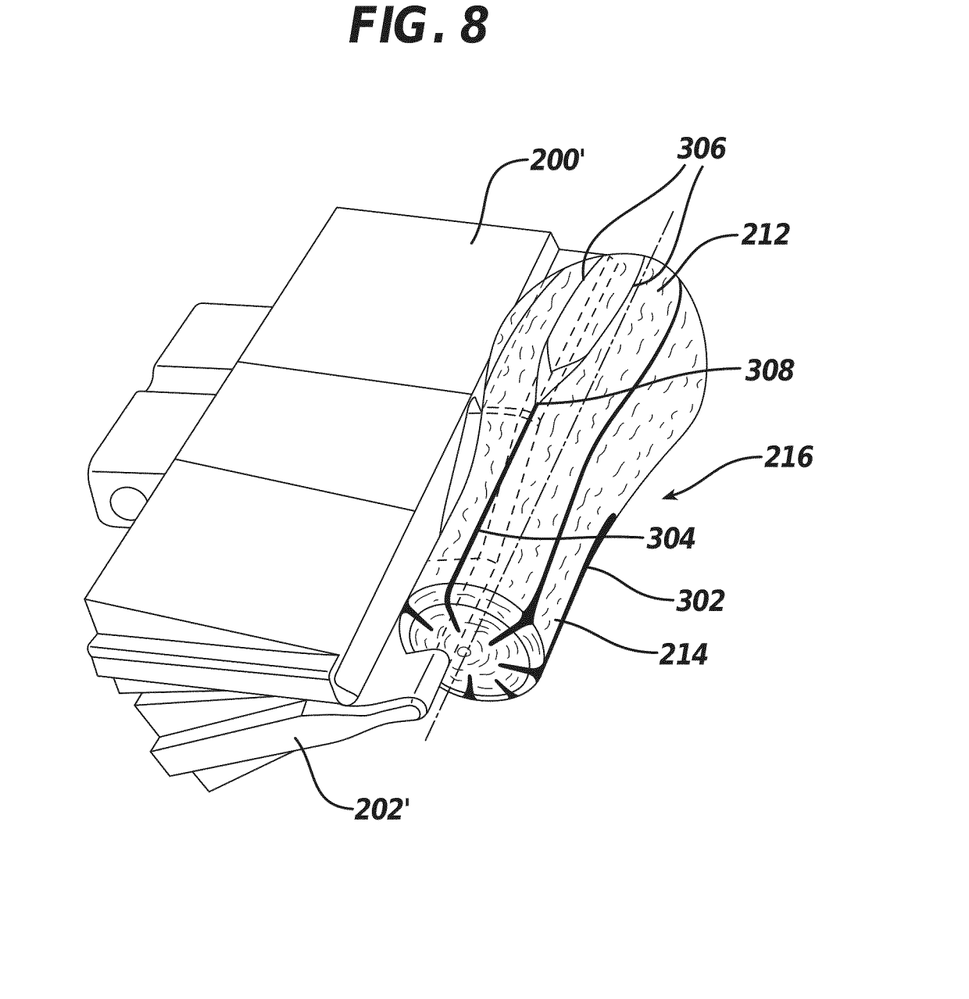
FIG. 8 is a perspective view of a composite penetrating die engaging with a tampon. Both front part and back part of the composites penetrating die are in a closed configuration, creating a substantially continuous groove made of two segments.
Figure 9:
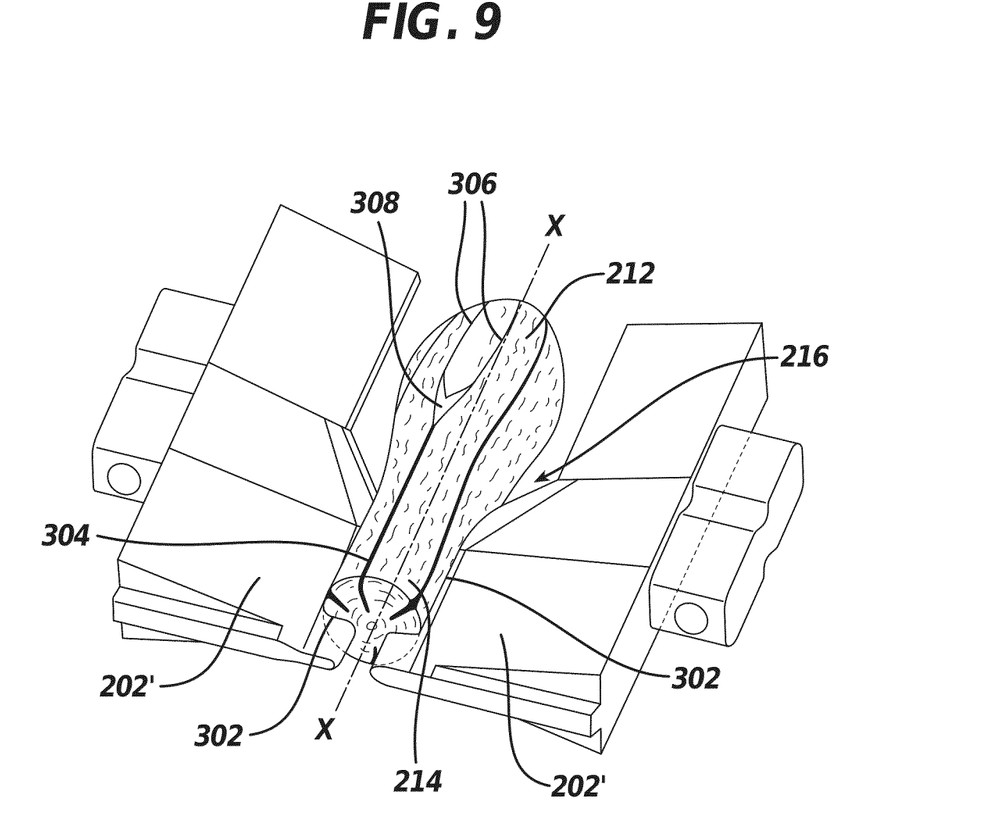
FIG. 9 is a perspective view of two back parts of composite penetrating dies engaging with a tampon.

Referring to FIGS. 8 and 9, two composite penetrating dies back parts 202', opposed to each other across the longitudinal axis X-X, are engaged in a tampon pledget 206. The grooves 302 created by the said two composite penetrating dies back parts 202' are located on the tampon 212 back portion 214a and have no continuity with any grooves located on the tampon front portion. They simply terminate in the central portion 216 of the tampon 212.

Figure 10:
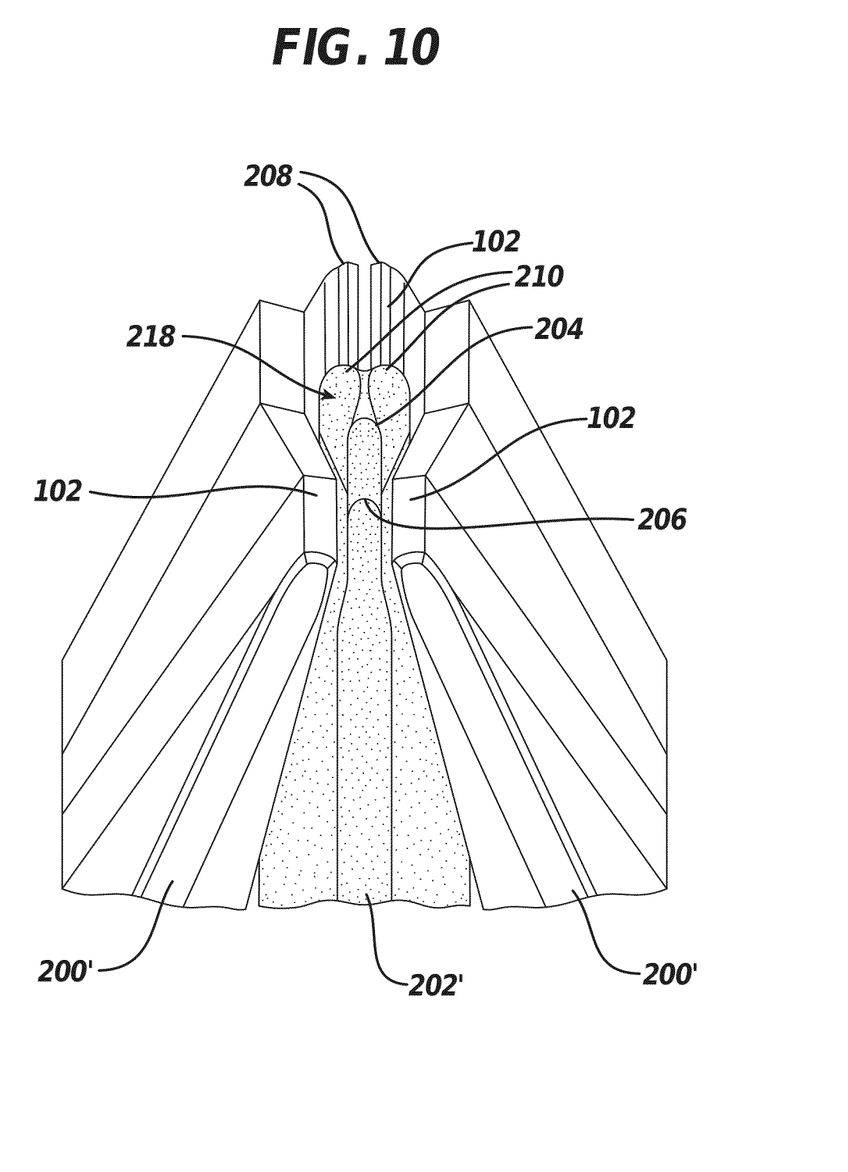
FIG. 10 is a perspective view of the front parts of two adjacent composite penetrating dies and the back part of one composite penetrating die positioned to produce a bifurcated groove on the outer surface of an absorbent tampon pledget. The composite penetrating die back part is represented at the forefront of the drawing and colored in grey.

Referring to FIG. 10, the pressing faces 102 of at least two adjacent composite penetrating die front parts 200' (also shown in FIGS. 8 and 9) and the pressing face of one composite penetrating die back part 202' (also shown in FIGS. 8 and 9) may be positioned to produce, on the outer surface of an absorbent tampon pledget, a bifurcated groove (shown in FIGS. 8 and 9) made of three segments: a back part groove segment 304 and two front part groove segments 306; the interior extremities of said three pressing faces are adjacent at a connection point 308 of the groove and in a location identified at cross-over point 218. In more detail three penetrating die: one penetrating die back part 202' and two penetrating die front parts 200' are shown in a closed position. Pressing face 102 extending between extremities 204, 206 of the composite penetrating die back part 202' is arranged and configured to form the withdrawal end portion 304 of the bifurcated, groove (See FIG. 8), and the pressing faces 102 extending between the two extremities 208, 210 of two associated composite penetrating die front parts 200' are arranged and configured to form the insertion end portion 306 (See FIG. 8) of the bifurcated groove.

A press according the present invention may comprise at least 2 sets of composites penetrating dies positioned to have their pressing faces producing at least two of said bifurcated grooves on the outer surface of an absorbent tampon pledget.

As used in the specification and the claims, the term "bifurcated", and variants thereof relate to a line that divides into two parts or branches such as in a "Y" shape.

In yet another embodiment of the present invention, the press may comprise at least two, preferably four, preferably six, and most preferably eight, of the composite penetrating die front parts having pressing faces with a shaped longitudinal profile.

Furthermore, a press according to the present invention may have composite penetrating die front parts comprising pressing faces with at least two different shaped longitudinal profile.

More particularly the shaped longitudinal profile of the pressing faces may be curved, creating a concave profile on the said pressing faces.

In a preferred embodiment, the present invention relates to a press, wherein the connection points of the two pressing faces of the said composite penetrating dies are positioned to produce a substantially continuous groove made of two segments, and the three pressing faces of the said composite penetrating dies positioned to produce a bifurcated groove made of three segments, are not all included in the same radial plane.

As used in the specification and the claims, the term "radial plane" and variants thereof relate to a plane perpendicular to the main longitudinal axis of the press.

Alternatively, the present invention may relate to a press, wherein the connection points of the two pressing faces of the said composite penetrating dies positioned to produce a substantially continuous groove made of two segments, and the three pressing faces of the said composite penetrating dies positioned to produce a bifurcated groove made of three segments, are all included in the same radial plane.

The position of the connection points of the different grooves that may be on the tampon pledget can have an influence on the flexibility of the said tampon. In certain circumstance it might be a benefit to provide a tampon with an improved flexibility, or in other words a tampon that could bend along its longitudinal axis. This type of tampons is believed to provide an increase comfort to the wearer.

A method for producing a shaped tampon pledget according to the present invention may comprise the steps of introducing a tampon blank in a press according to the present disclosure, actuating a first group of penetrating dies to compress the tampon blank with a first set of pressing faces, actuating a second group of penetrating dies to compress the tampon blank with a second set of pressing faces, partially disengaging one of the groups of penetrating dies to move the corresponding pressing faces in a transfer position, thus allowing the front portion of a compressed tampon pledget to pass through said partially disengaged group of penetrating dies, partially disengaging the second group of penetrating dies, and ejecting a resulting compressed tampon pledget from the press to a carrier device.

As used in the specification and the claims, the terms "partially disengaging" a group of penetrating dies mean that the said dies remain engaged with the front portion of the compressed tampon pledget but retract in a way sufficient to allow the ejecting device, for example an ejection rod, to push the compressed tampon pledget outside of the press without having said ejection device touching the penetrating dies.

A preferred method for producing a shaped tampon according to the present invention may comprise the steps of introducing a tampon blank in a press according to the present disclosure actuating the composite penetrating die front parts to compress the pledget front portion with the pressing faces of the composite penetrating dies front parts, actuating the composite penetrating die back parts to compress the pledget back portion with the pressing faces of the composite penetrating die back parts, partially disengaging the composite penetrating die back parts to release the pledget back portion from the pressing faces of the composite penetrating die back parts, partially disengaging the composite penetrating die front parts, evacuating the compressed tampon pledget from the press to a carrier device, fully disengaging the composite penetrating die front and back parts.

The composite penetrating die front parts of the present invention may be actuated in a non-simultaneous way. In other words, not all the penetrating die front parts are engaging the tampon blank at the same time. The space in the central cavity is limited and it might occur that in some configuration all the penetrating dies cannot be engaging fully with the tampon at the same time; in this case it is required that some of penetrating dies disengage, at least partially, before other penetrating dies can compress the tampon blank. The same configuration may occur for the penetrating die back parts, namely: the composite penetrating die back parts may be actuated in a non-simultaneous way.

In yet another embodiment, the invention may refer to a shaped catamenial tampon produced with a press as described in the present disclosure.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A method for shaping an absorbent tampon blank into a shaped tampon pledget, comprising the steps of:
   introducing a tampon blank having an outer surface and a front portion and a back portion into a press, comprising a central cavity arranged and configured to accommodate the absorbent tampon blank, the central cavity having a main longitudinal axis passing through the press; a plurality of penetrating dies, each penetrating die (i) having a first, straight portion, parallel to the main longitudinal axis and a second, curved portion with respect to the main longitudinal axis that creates a concave profile on the said pressing face, and (ii) having a pressing face on at least a fragment of its side facing the central cavity, and the plurality of penetrating dies being arranged radially around the said main longitudinal axis; at least one cam to actuate the plurality of penetrating dies, wherein:

a plurality of the said penetrating dies are divided longitudinally, creating a group of composite penetrating dies, said composite penetrating dies having two parts, a front part and a back part, and all the front parts of the composite penetrating dies constitute the front group and all the back parts of the composite penetrating dies constitute the back group and the front group and back group are actuated independently, at least one first penetrating die of the plurality of the said penetrating dies having a pressing face with a first shaped longitudinal profile, and at least one second penetrating die of the plurality of the said penetrating dies having a pressing face with a second shaped longitudinal profile, actuating the composite penetrating die front parts to compress the tampon blank front portion with the pressing faces of the composite penetrating dies front parts, and actuating the composite penetrating die back parts to compress the tampon blank back portion with the pressing faces of the composite penetrating die back parts to form the compressed, shaped tampon pledget, partially disengaging the composite penetrating die back parts to release the compressed, shaped tampon pledget back portion from the pressing faces of the composite penetrating die back parts, partially disengaging the composite penetrating die front parts, ejecting the compressed, shaped tampon pledget from the press to a carrier device, and fully disengaging the composite penetrating die front and back parts.

\* \* \* \* \*